United States Patent [19]

Vanlerberghe et al.

[11] Patent Number: 4,772,471

[45] Date of Patent: * Sep. 20, 1988

[54] AQUEOUS DISPERSIONS OF LIPID SPHERES AND COMPOSITIONS CONTAINING THE SAME

[75] Inventors: Guy Vanlerberghe, Commune de Villevaude; Rose-Marie Handjani, Paris, both of France

[73] Assignee: Societe Anonyme dite: L'Oreal, Paris, France

[*] Notice: The portion of the term of this patent subsequent to Aug. 12, 1997 has been disclaimed.

[21] Appl. No.: 102,935

[22] Filed: Dec. 12, 1979

Related U.S. Application Data

[63] Continuation-in-part of Ser. No. 865,499, Dec. 29, 1977, Pat. No. 4,217,344, which is a continuation-in-part of Ser. No. 700,038, Jun. 25, 1976, abandoned.

[30] Foreign Application Priority Data

Jun. 30, 1975 [FR] France .................................. 75 20456
Jun. 23, 1976 [BE] Belgium .............................. 0.168219
Nov. 15, 1977 [FR] France .................................. 77 34249

[51] Int. Cl.⁴ ........................ A61K 9/62; A61K 37/22; B01J 13/02
[52] U.S. Cl. ...................................... 424/450; 424/59; 424/62; 424/63; 424/89; 424/94.3; 424/498; 428/402.2; 428/402.21; 514/474; 514/887; 514/944
[58] Field of Search .................... 424/31, 32, 36, 38, 424/59, 62, 63, 89, 280, 351, 450, 498; 428/402.2, 402.21; 514/474

[56] References Cited

U.S. PATENT DOCUMENTS 3,041,289  6/1962  Katchen et al. ................. 264/4.3 X
3,630,920  12/1971  Freifeld et al. ....................... 252/90
3,686,701  8/1972  Charle et al. ................ 428/402.2 X
3,932,657  1/1976  Rahman .......................... 424/365 X
4,217,344  8/1980  Vanlerberghe et al. ......... 264/4.1 X

FOREIGN PATENT DOCUMENTS 2249552  5/1973  Fed. Rep. of Germany ... 428/402.2
1477048  3/1967  France ............................... 252/351

OTHER PUBLICATIONS

Ruckenstein et al.: "Thermodynamics of Amphiphilar Aggregation Into Micelles and Vesicles", Micellization, Solubilization, and Microemulsions, vol. 1, Edited by Mittal, Plenum Press, New York.
Israelachvili et al.: "Theory of Self-Assembly of Lipid Bilayers and Vesicles", Biochimica et Biophysica Acta, 470 (1977), 185-201.
Israelachvili et al.: "Theory of Self-Assembly of Hydrocarbon Amphiphiles Into Micelles and Bilayers", pp. 1526-1568, Rec'd. Nov. 7, 1975.
Hargreaves Thesis, "Monoalkyl Liposomes, Prebiotic Glycerolipids, and Possible Origins of Biological Membranes", 1978.
Sessa et al.: "Incorporation of Lysozyme Into Liposomes", J. of Biol. Chem., vol, 245, No. 13, Jul. 10, 1970, pp. 3295-3301.
Kinsky et al.: "Effect of Cholesterol Incorporation on the Sensitivity of Liposomes to the Polyene Antibiotic, Filipin", Biochim. Biophys. Acta, 152 (1968), 174-185.
Tanford: "The Hydrophobic Effect: Formation of Micelles and Biological Membranes", Wiley-Interscience Publ., John Wiley & Sons, New York, pp. 78 & 79.

Primary Examiner—Richard D. Lovering
Attorney, Agent, or Firm—Cushman, Darby & Cushman

[57] ABSTRACT

A dispersion in a continuous phase or spherules comprises arranged molecular layers of a non-ionic lipid compound encapsulating an aqueous phase wherein the non-ionic lipid compound has a lipophile group/hydrophile group ratio such that the non-ionic lipid compound swells in the aqueous phase to be encapsulated therein so as to form a lamellar phase. The hydrophile group of the non-ionic compound is selected from the group consisting of polyoxyethylene groups, polyglycerol groups and esters of polyols. The spherules have a diameter between 1,000 Å and 50,000 Å.

11 Claims, No Drawings

AQUEOUS DISPERSIONS OF LIPID SPHERES AND COMPOSITIONS CONTAINING THE SAME

This application is a continuation-in-part of our application Ser. No. 865,499, filed Dec. 29, 1977 and now U.S. Pat. No. 4,217,344, which, in turn, is a continuation-in-part of our application Ser. No. 700,038, filed June 25, 1976, now abandoned.

It is known that certain lipids possess the ability to form, in the presence of water, mesomorphic phases, the physical state of which is intermediate between a crystalline state and a liquid state. Certain known lipids which form a mesomorphic phase swell in an aqueous solution thereby forming spheres which are dispersed in an aqueous medium. These spheres comprise multimolecular layers, preferably bi-molecular layers, having a thickness approximately 30 to 100 Å (see, in particular, the article of Bangham, Standish and Watkins, J. Mol. Biol., 13, 238 (1965)).

Until now, it has only been possible to obtain this type of structure, in which a lipid bilayer encloses an aqueous internal space, by using ionic lipids, in particular, phospholipids which possess an ionic hydrophilic group and two hydrocarbon chains as a lipophilic group. The vesicles have a maximum diameter of 10,000 Å. The term liposomes refers to these microscopic phospholipid globules, preferably having a diameter of 300-1000 Å. The term "ufasomes" refers to vesicles formed from soaps of unsaturated fatty acids.

It has been proposed to employ the liposomes to encapsulate water-soluble active substances in aqueous compartments positioned between adjacent lipid layers thereby protecting the encapsulated active substances against exterior conditions (see, in particular, the article of Sessa and J. Weismann, J. Lipid Res., 9, 310 (1968) and the article of Magee and Miller, Nature, Vol. 235 (1972). See also U.S. Pat. No. 3,957,971 to Oleniacz, May 18, 1976.

The present invention relates to a dispersion of spherules, having a diameter between about 1000 Å and 50,000 Å, obtained with nonionic lipids and which, from this fact, form new compositions which enable the encapsulation of active substances, useful for example in pharmacy, in alimentation or in cosmetics. The non-ionic lipid compounds have a lipophile/hydrophile ratio such that the lipid compound swells in the aqueous phase to be encapsulated so as to form a lamellar phase; the hydrophilic groups of the non-ionic lipid compounds are polyoxyethylene groups, polyglycerol groups or other polyol groups.

The non-ionic lipid compounds are preferably selected from the group consisting of (1) ethers of linear, or branched, polyglycerol having the following respective formulas

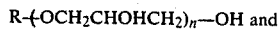

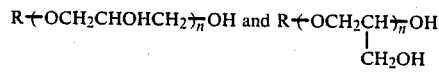

wherein n is a whole number between 1 and 6, R is selected from the group consisting of an aliphatic, linear or branched, saturated or unsaturated chain of 16 to 20 carbon atoms, the hydrocarbon radicals of lanolin alcohols and the 2-hydroxy alkyl residue of long chain α-diols;

(2) polyoxyethylenated fatty alcohols;
(3) the esters of polyols;
(4) natural or synthetic glycolipids, for example, cerebrosides.

It is clear that one will select, as a function of the active substance contained in the aqueous phase to be encapsulated, lipids which are capable of encapsulating in a stable manner the desired aqueous phase. To ensure that the lipids which constitute the lamellar phase provide stable spheres, it is necessary that there be sufficient lateral interaction between the lipid chains which, when placed side by side, constitute the layers of the spheres, that is, the Van der Waals forces between the chains must ensure sufficient cohesion between the layers. This condition is satisfied for lipids having the characteristics indicated above. The lipids usefully employed in the process according to the present invention belong to the class of water-in-oil type emulsifying agents.

Various additives can be combined with the non-ionic lipid compounds so as to modify its permeability characteristics or the superficial charge of said spheres. Representative additives include long chain alcohols and diols; sterols, for example, cholesterol; long chain amines and their quaternary ammonium derivatives; dihydroxyalkylamines; polyoxyethylenated fatty amines; esters of long chain amino alcohols, their salts and quaternary ammonium derivatives; phosphoric esters of fatty alcohols, for example, sodium dicetyl phosphate; alkylsulfates, for example, sodium cetyl sulfate; certain polymers such as polypeptides; and proteins.

The continuous phase of the dispersion, which surrounds the spheres, is an aqueous phase. The aqueous phase encapsulated within the spheres is an aqueous solution of the desired active substance and is preferably iso-osmotic relative to the continuous phase of the dispersion.

The aqueous phase to be encapsulated can include a wide variety of active substances. In particular, pharmaceutically active substances or alimentary substances or cosmetic substances can be employed. Cosmetic substances can include, for instance, components generally employed for the care of the skin and hair, including humectants, such as glycerine, sorbitol, pentaerythritol, inositol, pyrrolidone carboxylic acid and its salts; artificial tanning agents such as dihydroxy acetone, erythrulose, glyceraldehyde and γ-dialdehydes such as tartaric aldehyde, optionally in the presence of dyes; water-soluble sunscreen agents; antiperspirants; deodorants; astringents; skin refreshing products; tonics; cicatrisive products; keratolytic products; depilatories; perfumed water; extracts of animal or vegetable tissue; dyes; antipellicular agents; antiseborrheic agents; oxidizing agents (bleaching agents) such as $H_2O_2$; keratin reducing agents such as thioglycolic acid and its salts. Representative active pharmaceutical substances include vitamins; hormones; enzymes, for example, superoxide dismutase; vaccines; anti-inflammatory agents, for example, hydrocortisone; antibiotics; and bactericides.

In a preferred embodiment, the aqueous phase to be encapsulated is an aqueous solution of an active substance; the active substance in the aqueous phase to be encapsulated is a component exhibiting cosmetic activity; the continuous phase of the dispersion is an aqueous phase; the amount by weight of the spheres relative to the weight of the continuous phase of the dispersion is between about 0.01 and 0.5; and the continuous phase of the dispersion is advantageously isoosmotic relative to the aqueous phase encapsulated within the spheres.

The latter defined aqueous dispersions are quite desirable in the cosmetic field since the use of large dimensioned spheres substantially reduces or eliminates risk of the passage of these preparations into the body through the skin. Thus, there can be provided, in accordance with the present invention, products useful in the care of the skin and hair, for example, those containing humectants such as glycerin, sorbitol, pentaerythritol, inositol, pyrrolidone carboxylic acid and its salts; artificial bronzing agents such as dihydroxyacetone, erythrulose, glyceraldehyde and γ-dialdehydes such as tartaric aldehyde; skin coloring agents; water-soluble sunscreen agents; antiperspirants; deodorants; astringents; refreshing products; tonics; cicatrisants; keratolytics; depilatories; perfumed water; extracts of animal or vegetable tissue, such as proteins, polysaccharides and amniotic liquids; water soluble hair dyes; antipellicular agents; antiseborrheic agents; oxidizing agents (bleaching agents) such as $H_2O_2$; and reducing agents such as thioglycolic acid and its salts.

It will be noted that the use of aqueous dispersions according to the present invention in cosmetic preparations wherein the dispersions contain non-ionic lipid compounds provides a considerable advantage relative to the well known use of emulsions. Heretofore, when it was desired to employ preparations containing both fatty bodies and water, it was necessary in order to ensure the stability of the emulsion, to employ an amphiphile emulsifying agent. Further, it was known that certain emulsifying agents can be relatively irritating when applied to the skin. It has been discovered, during the course of work relative to the present invention, that this effect of emulsifying agents, for a given chemical structure, depends considerably on the form under which they are applied to the skin. Thus, it has been found that a water/oil emulsion composed of 42% perhydrosqualene, 8% emulsifying agent and 50% water is strongly irritating, whereas an 8% aqueous dispersion of the same emulsifying agent has a practically insignificant irritation index and that perhydrosqualene is absolutely inoffensive. From this it can be concluded that there is a synergy of irritation when an emulsifying agent is in the presence of an oil phase. The aqueous dispersions according to the present invention avoid the simultaneous use of an emulsifying agent and an oil, and this constitutes an important advance in the cosmetic field.

It will also be noted that there can be added to the dispersions of spheres according to the present invention various auxiliary components so as to modify the appearance of the organoleptic characteristics of the dispersions. Representative auxiliary components include opacifiers, gelling agents, aromatizing agents, perfumes or dyes.

In a general manner, the dispersions according to the present invention are particularly advantageous since they permit the introduction of hydrophilic substances into an essentially lipophilic medium. Under these circumstances, the hydrophilic components are protected from various agents which can alter their nature such as oxidizing agents, digestive juices and more generally those materials which are reactive with the thus encapsulated components. Further, the penetration and/or the fixation of the active substances can be modulated by varying the size of the spheres and their electric charge and their activity can also be deferred, delayed or retarded. Moreover, because they are masked or encapsulated, their organoleptic characteristics, in particular their taste, can be suppressed or sensibly altered. Finally, the lipids employed in these preparations possess, of themselves, such beneficial characteristics or emollient properties, lubricating qualities and lustering power.

Another embodiment of the present invention relates to the production of compositions of the type mentioned above, which that they are a mixture of at least two dispersions of spheres wherein the active substances contained in the aqueous phase encapsulated therein are different.

Advantageously, this embodiment provides a mixed system, i.e. a system where a dispersion of spheres containing a first type of active substance is combined with another dispersion containing a different but compatible or cooperative type of active substance, which permits the two types of substances to act simultaneously at the moment of treatment or use. Such a mixed system optionally provides a synergistic effect which would not be attained if the two types of active substances were employed separately.

The cosmetic composition according to this embodiment of the invention can result, for example, from a mixture of two dispersions of spheres, wherein the spheres of one dispersion contain in their encapsulated aqueous phase a sunscreen agent and the spheres of the other dispersion contain in their encapsulated aqueous phase a skin coloring agent. the sunscreen, 4-trimethylammonio benzylidene camphor methyl sulfate can be employed while the skin coloring agent can be a mixture of dihydroxyacetone and tartaric aldehyde. The said sunscreen and the skin coloring agent are encapsulated, separately, in spheres comprised of a non-ionic lipid material of the formula:

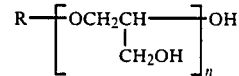

wherein R is hexadecyl and n has a statistical average value of 3.

In yet another embodiment of the present invention, the cosmetic composition can result from a mixture of two dispersions of spheres, wherein the spheres of one dispersion contain in their encapsulated aqueous phase, a sunscreen and the spheres of the other dispersion contain in their encapsulated aqueous phase a humectant. Representative sunscreen-humectant combinations include (a) an oxyethylenated derivative of para amino benzoic acid, as sunscreen, and sodium lactate as humectant wherein these cosmetically active substances are encapsulated, separately, in spheres comprising a non-ionic lipid material of the formula

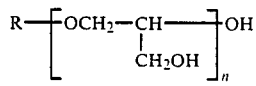

wherein R is hexadecyl and n is a number equal to 2;

(b) an oxyethylenated derivative of para amino benzoic acid, as the sunscreen, and the sodium salt of pyrrolidone carboxylic acid, as the humectant, wherein the sunscreen can be encapsulated in non-ionic lipid spheres of diglycerol oleate while the humectant can be encapsulated in non-ionic lipid spheres prepared from compounds of the formula

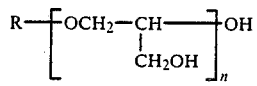

wherein R is hexadecyl and n has a statistical average value of 3; and

It has been observed that the combination of the two dispersions of spheres containing, respectively, a sunscreen and a humectant or skin coloring agent provides results superior to those achieved when the two said dispersions are employed separately.

The following study is provided to compare the significantly different properties of vesicles obtained from non-ionic materials and those produced from ionic materials. The study also illustrates that the properties of these spherules can depend on the size of the spheres, it being noted that (a) the permeability of ionic liposomes having a size larger or smaller than 1000 Å is greater than the permeability of non-ionic spherules having the same size; (b) the permeability of the non-ionic spherules increases less, as the time during which the dispersion is subjected to ultrasonic treatment increases, than the one of the ionic liposomes and (c) non-ionic spherules are capable of encapsulating a greater amount of a given solution to be encapsulated than ionic liposomes of essentially the same size.

In the following study, Parts I and II, the dispersions of the non-ionic and ionic spherules were prepared by dissolving the respective lipid material in a 2:1 mixture of chloroform and methanol; evaporating the solvent with a rotating evaporator with the last traces thereof being removed by passing the mixture through a blade pump; forming a 3% dispersion of the respective lipid materials in a 0.3M glucose solution, the dispersing operation being conducted at a temperature greater than the crystallization temperature of the lipid material employed; and cooling the resulting dispersion to ambient temperature with agitation.

Thereafter each dispersion, under a nitrogen atmosphere, was subjected to a conventional ultrasonic treatment for a period of 30 minutes at a temperature greater than the crystallization temperature of the lipids. Subsequently, each spherule dispersion was filtered on a column of Sephadex G50 coarse gel swollen in a 9% NaCl saline solution.

Part I—Permeability Study of Non-ionic and Ionic Spherules Prepared in Accordance with the Above Procedures In Table I, below, the permeability of the spherules relative to the encapsulated glucose is based on the amount of glucose passing out through the walls of the spherules and is expressed by the ratio of free glucose/total glucose and is calculated from dosages of free glucose and total glucose carried out one or several days after the filtration operation. The swelling data indicates the relative amount of glucose encapsulated and is expressed by the ratio of the weight of encapsulated glucose solution to the total weight of the spherules.

TABLE I

| Nature of Dispersion lipid composition in % | Non-Ionic Spherules Product of the formula $R+O-CH_2-CH)_n OH$ with $CH_2OH$ | | Ionic Spherules | | |
|---|---|---|---|---|---|
| | R = hexadecyl n = 2 | 45 | 47.5 | Egg Lecithin 85 | Egg Lecithin 75 | Egg Lecithin 54 |
| | cholesterol | 50 | 47.5 | Cholesterol 10 | Cholesterol 20 | Cholesterol 40 |
| | Sodium dicetyl phosphate | 5 | 5 | Sodium dicetyl phosphate 5 | Sodium dicetyl phosphate 5 | Sodium dicetyl phosphate 5 |
| Swelling %, | | 93 | 90 | 87 | 34 | 92 |
| Amount of leakage | | | | | | |
| 1 hr. | | 0.02 | 0.24 | | 0.40 | 0.08 |
| 18 hrs. | | 0.02 | 0.24 | 0.52 | 0.80 | 0.13 |
| 1 day | | | 0.35 | | 1.00 | 0.24 |
| 5 days | | 0.05 | 0.35 | | 1.00 | 0.48 |
| 7 days | | | | 1.00 | 1.00 | |
| Average size of spherules | | >>1000Å | ≤1000Å | >>1000Å* | ≤1000Å | >>1000Å* |

*choice between the two formulations

Part II—Permeability Study of Non-Ionic and Ionic Spherules Prepared in Accordance with the Above Procedures as a Function of Varying Ultrasonic Treatment Times In Table II below, the permeability of the spherules as a function of the length of time during which they are subjected to a conventional ultrasonic treatment increases as this length of time increases, it being noted, however, that this increase in permeability is significantly greater in the case of ionic spherules. It will also be noted from the swelling data tabulated below that as the ultrasonic treatment time increases, the non-ionic spherules encapsulate more glucose than the ionic spherules. Moreover, it can be seen from these data that the permeability of the spherules, ionic and non-ionic, is a function of their size, the spherules with the smaller diameter being more permeable than those having a larger diameter.

TABLE II

| Ionic Spherules | |
|---|---|
| Egg Lecithin | 85% |
| Cholesterol | 10% |
| Sodium dicetyl phosphate | 5% |
| Duration of Ultrasonics | |
| Minutes | Swelling, % | Amount of Leakage after one day |

TABLE II-continued

| 0  | 76 | 0.6 |
|----|----|-----|
| 5  | 44 | 0.5 |
| 20 | 33 | 1.0 |

Non-ionic Spherules

| | |
|---|---|
| Product of the general formula R$+$OCH$_2$—CH$\overline{)_n}$OH<br>                                                               CH$_2$OH<br>wherein R = alkyl radical of hydrogenated lanolin alcohols<br>n, having a statistical average value of 3 | 70% |
| Cholesterol | 20% |
| Sodium dicetyl phosphate | 20% |

Duration of Ultrasonics

| Minutes | Swelling, % | Amount of Leakage after one day |
|---------|-------------|--------------------------------|
| 0       | 80          | 0.0                            |
| 20      | 53          | 0.1                            |

The present invention further relates to a new industrial process for producing a dispersion of spherules, said spherules having a diameter between about 1,000–50,000 Å, constituted by lipid bilayers encapsulating an aqueous phase, said process comprising admixing at least one water-dispersible lipid having the formula X - Y wherein X represents a hydrophilic ionic or non-ionic group and Y represents a lipophilic group with an aqueous phase to be encapsulated in the spheres, wherein the lipophile/hydrophile ratio of the lipid is such that the lipid swells in the aqueous phase to be encapsulated so as to form a lamellar phase; agitating the resulting mixture so as to assure the production of said lamellar phase; adding a liquid dispersion phase in an amount greater than the quantity of lamellar phase obtained, said dispersion liquid being other than said aqueous phase to be encapsulated so that when the resulting mixture is shaken, the said lamellar phase is transformed into said spheres in the presence of said dispersion liquid; and vigorously shaking the resulting mixture for a period of time ranging from 15 minutes to about 3 hours whereby said spheres are formed. The dispersion can be ultimately submitted to an ultrasonic treatment.

In a preferred embodiment, the weight ratio of the amount of aqueous phase to be encapsulated which is admixed with the lipids, to the amount of lipids forming the lamellar phase is between about 0.1 and about 3; the aqueous phase to be encapsulated within the spheres can be water or an aqueous solution of an active component; the weight ratio of the amount of liquid dispersion phase to the amount of the lamellar phase which is dispersed therein is between about 2 and about 100; the liquid dispersion phase and the aqueous phase to be encapsulated are, preferably, iso-osmotic; the liquid dispersion phase can advantageously be an aqueous solution. The agitation procedures which are effected as the last step of the present process are advantageously effected by means of a shaker agitator. The process is carried out at ambient temperature or at a more elevated temperature if the lipid is solid at ambient temperature. Where it is desired to obtain spheres having an average diameter less than 1000 Å, the resulting dispersion of spheres can be subjected to an ultra-sonic treatment.

To form the lamellar phase, a single lipid material or a mixture thereof can be employed. The lipids employed have a long saturated or unsaturated, branched or linear lipophilic chain having from 12 to 30 carbon atoms such as oleic, lanolic, hexadecylic and isostearylic. When the X - Y compound forming the lamellar phase is a non-ionic one, it can be a polyoxyethylene, ethylenated fatty alcohol, a linear or branched polyglycerol ether, a polyol ester or a natural or synthetic glycolipid. When the X - Y compound forming the lamellar phase is an ionic one, it can be an amphoteric compound having two lipophilic chains or an association of two long chain organic ions of opposite signs. Very satisfactory results have been obtained by using as the lipids forming the lamellar phase ethers of polyglycerol, such as those which are described in French Patents Nos. 1,477,048 and 2,091,516 and in the patent of addition 94,928.

The present invention overcomes the disadvantages of known processes for the preparation of liposomes which render them difficult to put into practice on an industrial scale.

One process consists in dissolving lipids in a volatile solvent, forming a thin film of lipids on the wall of a flask by evaporating the solvent, introducing the liquid to be encapsulated and submitting the flask to vigorous or ultrasonic vibrations to provide the dispersion.

Another process consists in placing the lipids, when they are liquids, in contact with the aqueous solution to be encapsulated and submitting the mixture to vigorous agitation or ultrasonic treatment.

A French application, No. 76.02016, discloses a method of preparing a liquid pharmaceutical composition capable of releasing a product at a regulated speed, by uniformly dispersing a phospholipid in water to produce an aqueous dispersion of phospholipid; adding a medicament to this aqueous dispersion of the phospholipid or by dissolving the medicament therein; congealing the thus obtained aqueous dispersion so as to enclose the medicament in the lipid spherules; and then decongealing the cooled dispersion so as to obtain an aqueous suspension of the medicament enclosed in the lipid spherules.

All these processes require the use of a total volume of the liquid which has to be encapsulated (confined within the interior of lipid spherules) very much larger than the volume of the liquid which is finally contained in the spherules. Removal of non-encapsulated solution by different techniques is quite impossible in an industrial scale: purification by elution of spherules on a "Sephadex or Sepharose" type separation column leads to an extremely dilute dispersion and to a loss of "active" non-encapsulating substance, centrifugation with the supernatant being pipetted off and followed by resuspension of liposomes in normal saline, performed a plurality of times to insure complete removal of non-encapsulated solution is time consuming and can be applied only to spherules having large diameters (10,000 Å).

The present invention overcomes these disadvantages and permits to prepare on a large scale (thousands of pounds) a dispersion of concentrated spherules without any solvent, even when solid lipids are used.

EXAMPLE 1

In a 50 ml round flask, placed on a water bath maintained at 55° C., 500 mg of a product having the formula

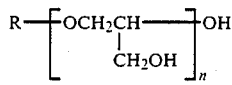

wherein R is hexadecyl and n is 2, are mixed with 10 ml of a 0.3M aqueous solution of methionine. The mixture is homogenized at 55° C.

The flask, placed on a shaker, is vigorously agitated for 3 hours at 55° C.

The resulting dispersion is clear. The diameter of the spheres in the dispersion is about 10,000 Å. On cooling the dispersion to ambient temperature, a white gel is obtained.

EXAMPLE 2

In a 50 ml round flask, 500 mg of a product having the formula

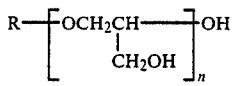

wherein R is the alkyl residue of isostearyl alcohol and n has a statistical average value of 2, are mixed with 5 ml of water. The resulting mixture is homogenized at ambient temperature The flask, placed on a shaker, is vigorously agitated for 4 hours.

The resulting dispersion is milky and the diameter of the spheres therein is about 50,000 Å.

The dispersion can be submitted to an ultra-sonic treatment to reduce significantly the size of the spheres.

EXAMPLE 3

In a 50 ml round flask, 80 mg of a product having the formula

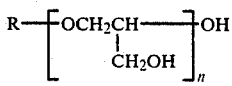

wherein R is hexadecyl and n is 2, 10 mg of cholesterol and 10 mg of dicetyl phosphate are dissolved in 2 ml of a 2:1 mixture of chloroform and methanol. The solvent is then evaporated with a rotating evaporator and the last traces of the solvent are removed by passing the mixture through a blade pump for 1 hour. To this lipid material there are added 10 ml of a 0.15M aqueous solution of the sodium salt of pyroglutamic acid. The flask, placed on a shaker, is vigorously agitated for 2 hours on a water bath maintained at 55° C. Then the same is progressively cooled down to ambient temperature.

The dispersion is submitted to an ultra-sonic treatment for 1 hour at a temperature close to ambient temperature. The dispersion is then filtered on a column of Sephadex G50 coarse gel swollen in distilled water.

The resulting dispersion is fluid and clear after the ultrasonic treatment and the diameter of the spheres therein is lower than 10,000 Å.

EXAMPLE 4

In a 50 ml round flask, 190 mg of a product of the formula

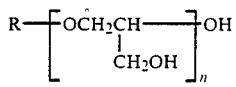

wherein R is the alkyl residue of hydrogenated lanolin alcohols and n has a statistical average value of 3, 100 mg of cholesterol and 20 mg of dicetyl phosphate are dissolved in 3 ml of a 2:1 chloroform-methanol mixture. The solvent is then evaporated with a rotating evaporator and the last traces of the solvent are removed by passing the mixture through a blade pump. To this lipid material there are added 5 ml of a 8.4% solution of the triethanolamine salt of urocanic acid at a temperature of 70° C. The flask, placed on a shaker, is vigorously agitated for 2 hours at 70° C. Then the same is progressively cooled down to ambient temperature. The resulting fluid dispersion contains spherules having a diameter of about 20,000 Å.

EXAMPLE 5

In a 50 ml round flask, 200 mg of a product of the formula

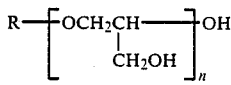

wherein R is hexadecyl and n is 2, 25 mg of cholesterol and 25 mg of dicetyl phosphate are intimately mixed. To the resulting mixture there is added 0.3 ml of a 10% solution of tartaric aldehyde and the same is then homogenized at 55° C. To the resulting homogeneous mixture there are added 4.7 ml of a 0.145M NaCl solution.

The flask, placed in a water bath, is vigorously agitated with a shaker for 2 hours at 55° C. and then progressively cooled down to ambient temperature.

The resulting dispersion is gelled and has a slightly bluish appearance.

The simultaneous application on the skin of this dispersion of niosomes and an aqueous solution at the same final concentration of tartaric aldehyde, permits to appreciate two effects of the niosomes, i.e. they substantially improve the color developed and they clearly improve the resistance of this coloration to washing with water and detergents.

EXAMPLE 6

In a 50 ml round flask, 380 mg of a product of the formula

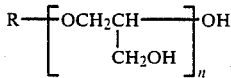

wherein R is hexadecyl and n is equal to 2, 80 mg of cholesterol and 20 mg of dicetyl phosphate are dissolved in 5 ml of a 2:1 chloroform-methanol mixture. The solvent is then evaporated with a rotating evaporator and the last traces of solvent are removed by passing the mixture through a blade pump for 1 hour. To this lipid material there are added at a temperature of 70° C., 5 ml of a 4% solution of paraaminobenzoic acid oxyethylenated with 25 moles of ethylene oxide. The flask, placed on a shaker, is vigorously agitated for 2 hours at 70° C. and then progressively cooled down to ambient temperature. The resulting spheres have an average diameter less than 10,000 Å.

Essentially the same procedures noted above are repeated except that the oxyethylenated paraaminobenzoic acid is replaced with sufficient 2% solution of sodium lactate to provide 5 ml of a dispersion containing spheres encapsulating said sodium lactate.

The two dispersions of spheres thus produced are then admixed with slight agitation at ambient temperature.

EXAMPLE 7

In a 50 ml round flask there are mixed 300 mg of diglycerol oleate, 100 mg of cholesterol and 40 mg of dicetyl phosphate. To the resulting mixture there is added 0.6 ml of a 2% solution of paraaminobenzoic acid oxyethylenated with 25 moles of ethylene oxide. This mixture is then homogenized and to the homogeneous mixture there are added 4.4 ml of a 0.9% solution of NaCl at a temperatue of 40° C. The flask placed on a shaker, is vigorously agitated for 2 hours at 40° C. and then progressively cooled down to ambient temperature.

In a separate 50 ml round flask, 166 mg of a product of the formula

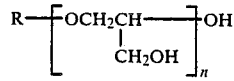

wherein R is hexadecyl and n has a statistical average value of 3, 166 mg of cholesterol and 17 mg of dicetyl phosphate are thoroughly mixed. To this lipid mixture there is added 0.4 ml of a 2% solution of the sodium salt of pyrrolidone carboxylic acid. The mixture is then homogenized and to the homogeneous mixture there are added 4 ml of a 0.9% solution of NaCl at 70° C. The flask, placed on a shaker, is vigorously agitated for 2 hours at 70° C. and then progressively cooled down to ambient temperature.

The two dispersions of spheres thus produced are then admixed with slight agitation at ambient temperature.

EXAMPLE 8

In a 50 ml round flask, 380 mg of a product of the formula

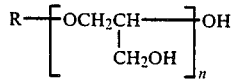

wherein R is hexadecyl and n has a statistical average value of 3, 380 mg of cholesterol and 40 mg of dicetyl phosphate are thoroughly mixed. To this lipid material there are added 3.3 ml of a 4% solution of 4-trimethylammonio benzylidene camphor methyl sulfate. The resulting mixture is homogenized and to the homogeneous mixture there are added 6.7 ml of a 0.9% solution of NaCl at a temperature of 70° C. The flask, placed on a shaker, is vigorously agitated for 2 hours at 70° C. and is then progressively cooled down to ambient temperature. The resulting spheres have an average diameter of 20,000 Å.

In a separate 50 ml round flask, 180 mg of a product of the formula

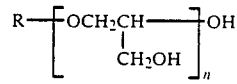

wherein R is hexadecyl and n has a statistical average value of 3, 180 mg of cholesterol and 40 mg of dicetyl phosphate are thoroughly mixed. To this lipid material there are added 0.8 ml of a 3% solution of dihydroxy acetone and 1.5% tartaric acid. The resulting mixture is homogenized and to the homogeneous mixture there are added 4.2 ml of a 0.9% solution of NaCl at a temperature of 70° C. The flask, placed on a shaker, is vigorously agitated for 2 hours at 70° C. and is then progressively cooled down to ambient temperature. The resulting spheres have a diameter of about 10,000 Å.

The two dispersions of spheres, thus produced and containing respectively a sunscreen agent and a skin coloring agent, are then admixed with slight agitation, at ambient temperature.

EXAMPLE 9

In a 50 ml round flask, 500 mg of a product having the formula

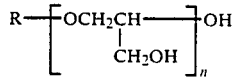

wherein R is hexadecyl and n is 2 are mixed with 0.335 ml of a 0.3M aqueous solution of cysteine. The resulting mixture is homogenized at 55° C.

There are then added 4.1 ml of a 0.145M KCl solution. The flask, placed on a shaker, is vigorously agitated for 3 hours.

The resulting dispersion is practically clear at 55° C. The diameter of the spheres contained therein is about 20,000 Å. On slowly cooling the dispersion to ambient temperature, a white, opaque gel is produced.

The dispersion withdrawn at 55° C. can be diluted with a solution, iso-osmotic or not, containing a thickening agent such as a gum or a polymer to provide a slightly opaque solution. The amount of dilution depends upon the desired appearance of the dispersion.

EXAMPLE 10

In a 50 ml round flask, 500 mg of a product having the formula

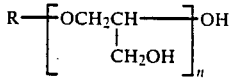

wherein R is the alkyl residue of hydrogenated lanolin alcohol, and n has a statistical average value of 3, are mixed with 0.220 ml of a 0.5M aqueous solution of pentaerythritol. The resulting mixture is homogenized at ambient temperature.

There are then added 4 ml of water. The flask, placed on a shaker, is vigorously agitated for 30 minutes.

The resulting dispersion has a milky appearance and the diameter of the spheres therein is greater than 10,000 Å.

EXAMPLE 11

In a 50 ml round flask, 500 mg of a product of the formula

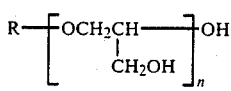

wherein R is hexadecyl and n has a statistical average value of 3 are mixed with 0.5 ml of a solution containing 50 mg/ml of a protein having a molecular weight of about 10,000 and sold under the mark "CROTEINE C". The mixture is homogenized at 60° C. To the homogenized mixture there are added 4 ml of a 0.145M KCl solution. The flask, placed on a shaker, is vigorously agitated for 3 hours.

The resulting dispersion is clear and the diameter of the spheres therein is about 10,000 Å. On slowly cooling the dispersion to ambient temperature, a white opaque gel is obtained.

EXAMPLE 12

In a 50 ml round flask, 300 mg of a product, obtained by molecular distillation, having the formula

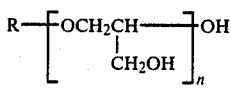

wherein R is the alkyl residue of oleyl alcohol and n is 2, are intimately mixed with 150 mg of cholesterol and 50 mg of an amine of the formula

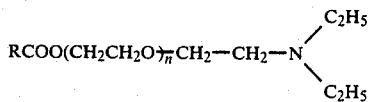

wherein RCOO is the residue of copra and n is a number between 2 and 5. To the resulting mixture there is added 0.5 ml of a 0.3M aqueous solution of sorbitol and the same is then homogenized at ambient temperature.

There are then added 4 ml of a 0.145M KCl solution to the homogeneous mixture and the flask, placed on a shaker, is vigorously agitated for 4 hours.

The resulting dispersion is opalescent and the diameter of the spheres therein is about 20,000 Å.

EXAMPLE 13

In a 50 ml round flask, 250 mg of oleyl alcohol oxyethylenated with 10 moles of ethylene oxide (sold under the mark "BRIJ 96") are intimately mixed with 250 mg of oleyl alcohol oxyethylenated with 2 moles of ethylene oxide (sold under the makr "BRIJ 92"). To the resulting mixture there is added 1 ml of a 0.5M aqueous solution of glycerol and the resulting admixture is homogenized at ambient temperature.

There are then added 20 ml of a 0.145M NaCl solution. The flask, placed in a shaker, is vigorously agitated for 1 hour.

The resulting dispersion is fluid and milky and the diameter of the spheres therein is about 10,000 Å.

EXAMPLE 14

In a 50 ml round flask, 500 mg of tetraethylene glycol monolauryl ether are mixed with 0.4 ml of a 0.3M aqueous solution of glucose. The resulting mixture is homogenized at ambient temperature.

To the mixture there are then added 5 ml of a 0.145M KCl solution. The flask, placed on a shaker, is vigorously agitated for 15 minutes.

The resulting dispersion is clear, and the diameter of the spheres therein is about 10,000 Å.

EXAMPLE 15

In a 50 ml round flask, 300 mg of sphingomyelin are mixed with 0.350 ml of a 0.3M aqueous solution of glucose. The resulting mixture is homogenized at ambient temperature.

There are then added 5 ml of a 0.145M NaCl solution and the flask, placed on a shaker, is vigorously agitated for 2 hours.

The resulting dispersion is milky and the diameter of the spheres therein is about 20,000 Å.

The dispersion can be submitted to an ultrasonic treatment for 1 hour to reduce the diameter of the spheres.

EXAMPLE 16

In a 50 ml round flask, 300 mg of sphingomyelin are mixed with 0.350 ml of a 0.3M aqueous solution of ascorbic acid. The resulting mixture is homogenized at ambient temperature.

To the resulting homogeneous mixture there are added 2.650 ml of a 0.145M NaCl solution. The flask is then placed on a shaker and vigorously agitated for 4 hours.

The resulting dispersion is milky and the diameter of the spheres therein is about 20,000 Å.

What is claimed is:

1. A dispersion in a continuous phase of spherules comprising arranged molecular layers of a non-ionic lipid compound encapsulating an aqueous phase wherein the non-ionic lipid compound has a lipophile group/hydrophile group ratio such that the non-ionic lipid compound swells in the aqueous phase to be encapsulated therein so as to form a lamellar phase, the hydrophile group of said nonionic compound being selected from the group consisting of polyoxyethylene groups, polyglycerol groups and other polyol groups, said spherules having a diameter between 1,000 Å and 50,000 Å.

2. The dispersion of claim 1 wherein the non-ionic lipid compound is selected from the group consisting of
   (1) linear or branched polyglycerol ethers having, respectively, the formulas R-(-OCH$_2$CHOHCH$_2$-)$_n$ OH and

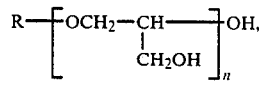

wherein n is a whole number between 1 and 6, R is selected from the group consisting of a linear or branched, saturated or unsaturated aliphatic chain having 16 to 20 carbon atoms, the hydrocarbon residue of lanolin alcohols and the 2-hydroxy alkyl residue of long chain α-diols,
   (2) polyoxyethylenated fatty alcohols,
   (3) esters of polyols, and
   (4) natural or synthetic glycolipids.

3. The dispersion of claim 1 wherein said non-ionic lipid is combined with an additive selected from the group consisting of a long chain alcohol or diol; a sterol; a long chain amine or the quaternary ammonium derivative thereof; a dihydroxyalkylamine; a polyoxyethylenated fatty amine; an ester of a long chain amino alcohol, a salt thereof or a quaternary ammonium derivative thereof; a phosphoric ester of a fatty alcohol; an alkyl sulfate; a polypeptide and a protein.

4. The dispersion of claim 1 wherein said continuous phase is an aqueous phase.

5. The dispersion of claim 1 wherein said aqueous phase encapsulated in said spherules is an aqueous solution of an active compound.

6. The dispersion of claim 1 wherein said aqueous phase encapsulated in said spherules is iso-osmotic relative to the said continuous phase of said dispersion.

7. The dispersion of claim 1 wherein said aqueous phase encapsulated in said spherules is an aqueous solution of a component exhibiting cosmetic activity.

8. The dispersion of claim 1 wherein said aqueous phase encapsulated in said spherules is an aqueous solution of at least one pharmaceutically active substance.

9. The dispersion of claim 8 wherein said pharmaceutically active substance is selected from the group consisting of vitamins, hormones, enzymes, vaccines, anti-inflammatory agents, antibiotics and bactericides.

10. The dispersion of claim 1 wherein said aqueous phase encapsulated in said spherules is an aqueous solution of at least one alimentary substance.

11. The dispersion of claim 1 wherein the weight of the spherules relative to the weight of the continuous phase is between 0.01 to 0.5.

* * * * *